United States Patent [19]

Ifuku et al.

[11] Patent Number: 5,885,792
[45] Date of Patent: Mar. 23, 1999

[54] BIOTIN OPERON

[75] Inventors: Ohji Ifuku; Shinitiro Haze; Jiro Kishimoto, all of Yokohama; Kazuo Nakahama, Nagaokakyo, all of Japan

[73] Assignee: Shiseido Company, Ltd., Tokyo, Japan

[21] Appl. No.: 944,259

[22] Filed: Sep. 14, 1992

[30] Foreign Application Priority Data

Sep. 13, 1991 [JP] Japan ................................. 3-235148

[51] Int. Cl.⁶ ........................... C12N 15/31; C12N 15/70; C12N 15/11
[52] U.S. Cl. ................ 435/69.1; 435/172.3; 435/252.33; 435/320.1; 536/23.1; 536/23.7
[58] Field of Search ................................... 435/69.1, 119, 435/252.33; 536/23.1, 24.1, 23.7

[56] References Cited

FOREIGN PATENT DOCUMENTS

| 2216530 | 10/1989 | United Kingdom . |
| 8701391 | 3/1987 | WIPO . |
| 8904365 | 5/1989 | WIPO . |

OTHER PUBLICATIONS

G. Ketner et al., "Operator and Promotoer Mutations Affecting Divergent Transcription in the bio Gene Cluster of *Escherichia coli*", J. Mol. Biol. (1975) vol. 96, pp. 13–27.

Chemical Abstracts, vol. 108, No. 15, Apr. 11, 1988, Abstract No. 125889, p. 199.

Otsuka et al., "The Regulatory Region of the Biotin Operon in *Escherichia coli*", Nature, vol. 276 Dec. 14, 1978, pp. 689–694.

Otsuka et al., "The *Escherichia coli* Biotin Biosynthetic Enzyme Sequences Predicted from the Nucleotide Sequence of the . . . ", J. Biol. Chem., vol. 263, No. 36, Dec. 25, 1988, pp. 19577–1958.

Barker et al., "Sequence and Properties of Operator Mutations in the Bio Operon of *Escherichia coli*", Gene, vol. 13, pp. 89–102, 1981.

*Primary Examiner*—John LeGuyader
*Attorney, Agent, or Firm*—Foley & Lardner

[57] ABSTRACT

A DNA sequence of high biotin operon-expression system usable for breeding a bacterium having excellent biotin productivity is provided.

A DNA sequence of biotin operon characterized in the fact that at least one base pair of either a nucleotide sequence of the regulatory region of the biotin operon of *Escherichia coli* or a nucleotide sequence in the vicinity of the bioB initiating codon is mutated in comparison with that of the one in its wild type strain is provided. *Escherichia coli* transformed with a recombinant plasmid carrying such a DNA sequence has high biotin-productivity.

3 Claims, 2 Drawing Sheets

Fig.2

```
            ─────────── ──    *    ──   ──────────
      GACTTGTAAACCAAATTGAAAAGATTTAGGTTTACAAGTC
      CTGAACATTTGGTTTAACTTTTCTAAATCCAAATGTTCAG
      ─────────── ──        ──   ──────────
```

BIOTIN OPERON

BACKGROUND OF THE INVENTION

1. Field of Invention

This invention relates to *Escherichia coli*, and particularly to a DNA sequence of biotin operon in which a base pair of either a nucleotide sequence of the regulatory region of the biotin operon of *Escherichia coli* or a nucleotide sequence in the vicinity of the bioB initiation codon is mutated in comparison with that of its wild type strain. According to such a DNA sequence, a system for highly expressing biotin operon can be constructed.

2. Description of Related Art

In the production of biotin, which is a vitamin required for animals, plants, and microorganisms, in order to substitute chemical synthetic processes involving complicated steps, effective processes utilizing a fermentation process employing microorganisms improved by genetic engineering techniques, etc. have been developed (see, for example, Japanese Unexamined Patent Publication (Kokai) No. 61-149091 and EP-A-0316229).

As highly producing strains in which a microorganism is improved to enhance the productivity of a specific useful substance, in the case where there exists a feedback repression mechanism to an enzyme synthesizing system by the final product, repressor mutants and operator mutants produced by mutation can be mentioned. Also, strains where their promotor activity per se in the enzyme synthesizing system has been reinforced have been suggested. In the case of fully making use of genetic engineering technology, there are also processes where an enzyme synthesizing system is ligated to a highly expressing promotor different from its original promotor. The repressor mutants relating to highly biotin producing strains include, for example, DRK 332 strain (FERM P-8585, Japanese Unexamined Publication (Kokai) No. 155081), and an example of using a highly expressing promoter with genetic engineering technology is a strain where only bioB gene is reinforced using a $P_L$ promotor (Japanese Unexamined Publication (Kokai) No. 61-149091), etc.

Although all of the above-enumerated microorganisms having been improved for the purpose of increasing biotin productivity have attained their desired objects, there is still room for improvement, and a necessity for providing further improved strains with high biotin productivity still remains in order to improve the productivity of biotin by fermentation methods. In the biotin operon of *Escherichia coli*, five genes, i.e., bioA, bioB, bioF, bioC, and bioD contributing to the biotin biosynthesis are coded. The regulatory region which controls their expression locates between bioA and bioB, and bioA is coded in the left chain, while bioB, bioF, bioC, and bioD are coded in the right chain. They are subjected to transcription in the reverse direction, respectively, and the transcription in both directions is controlled by one operator. The transcription mechanism in both directions is also one reason why the alternation into a highly expressing promotor by genetic engineering technology cannot be simplified. In spite of this, it is important for improving the productivity of biotin to attain a high expression of the biotin operon. Several reports have been made for the mutation of the operator (*Nature*, 276, 689 (1978), *Gene*, 13, 89 (1981)), but there is no mention about the productivity of biotin. In some cases, the promotor activity overlapping with the operator region is significantly decreased.

SUMMARY OF THE INVENTION

The object of the present invention is to construct a highly expressing system of biotin operon by causing a mutation completely different than the conventional mutation at the position of the regulatory region of the biotin operon or the position in the vicinity thereof, and to provide a high biotin-producing strain having the same.

The present inventors have repeatedly searched for a way to improve *Escherichia coli* to enhance biotin productivity. As a result, it has been found that when a mutation is induced at a position completely different than that of the conventional position within the biotin operon regulatory region or the position in the vicinity thereof, a high biotin operon expressing system can be constructed. Specifically, when antimetabolites which are biotin analogues are utilized and mutants having resistance to the analogues are selected, mutants having significantly enhanced productivity of biotin vitamers are found from these mutants in a high frequency. It has been further found that from these mutants, ones in which mutations have been induced at the biotin operon regulatory region or a specific region in the vicinity thereof can be obtained in a further high frequency can be attained. Still further, it has been found that these mutations can promote a high expression of biotin operon, resulting in a significant enhancement of the productivity of biotin vitamers, thereby achieving this invention.

That is, there is provided a DNA sequence in which a nucleotide sequence of the biotin operon regulatory region or a specific region residing in the vicinity of the bioB initiation codon has been mutated in comparison with that of its wild type strain. This sequence is characterized in the fact that at least one base pair of either a nucleotide sequence of the regulatory region of the biotin operon of *Escherichia coli* or a nucleotide sequence in the vicinity of the bioB initiation codon is mutated in comparison with that of its wild type strain. More specifically, the mutation resides within the operator, or at least one base pair at a plurality of positions before and after the bioB initiation codon has been mutated. Such an operon becomes a high biotin expression.

According to the present invention, there is also provided a process for producing biotin characterized by culturing microorganisms belonging to genus Escherichia having been transformed with recombinant plasmid carrying the DNA sequence having been mutated as described above in a nutrient medium, and collecting the accumulated biotin in the culture broth.

According to the present invention, a novel DNA sequence which can be advantageously utilized for producing biotin vitamers is provided, from which microorganisms having these biotin operons and having improved productivity of biotin vitamer can be obtained. The microorganisms are transformed with the recombinant plasmid containing biotin operon, contained therein can be advantageously used in the production of biotin vitamer.

BRIEF DESCRIPTION OF DRAWINGS

The present invention will be illustrated by referring to the drawings attached to the specification.

DESCRIPTION OF THE PREFERRED EMBODIMENT

CONCRETE EMBODIMENTS AND FUNCTION

The biotin operon in accordance with the present invention is a biotin operon of *Escherichia coli*, and has a cluster of five genes biotin biosynthetic enzymes i.e., bioA, bioB, bioF, bioC, and bioD. The term "biotin operon regulatory region" is located in sequence No. 1 (SEQ ID NO:1) of Sequence Listing showing the right chain locating between bioA and bioB, and more specifically it means a region from the −1st nucleotide pair to the 86th base pair, taking A of the bioB initiation codon, ATG, as the first position in the base sequence shown in FIG. 1. Also, the term "region in the vicinity of the bioB initiation codon" means a region from the first base pair to the sixth base pair, taking A of the bioB initiation codon, ATG, as the first position.

Figure 1:
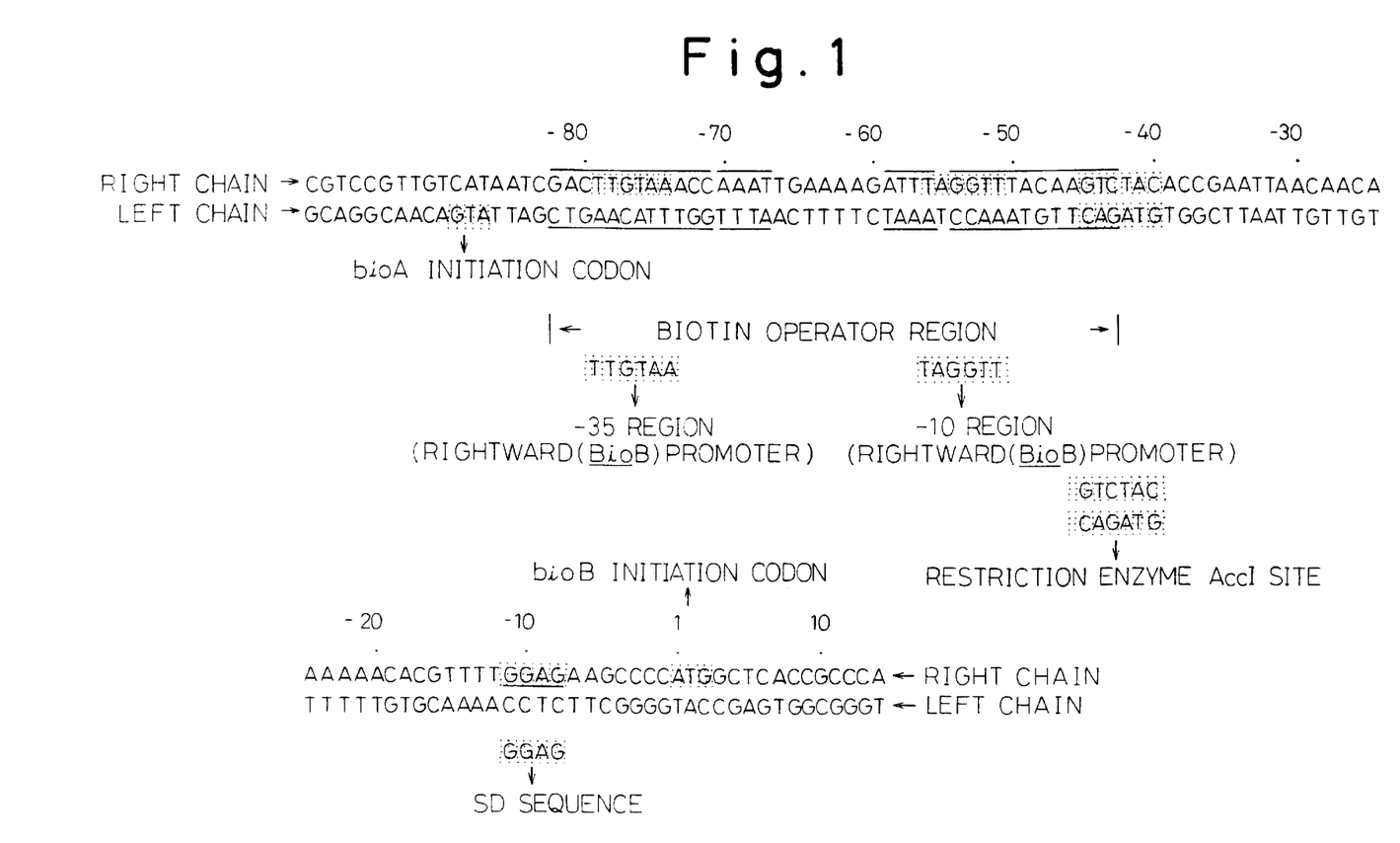
FIG. 1 shows the nucleotide sequence in or near the regulatory region of biotin operon and its characteristic site.
Figure 2:
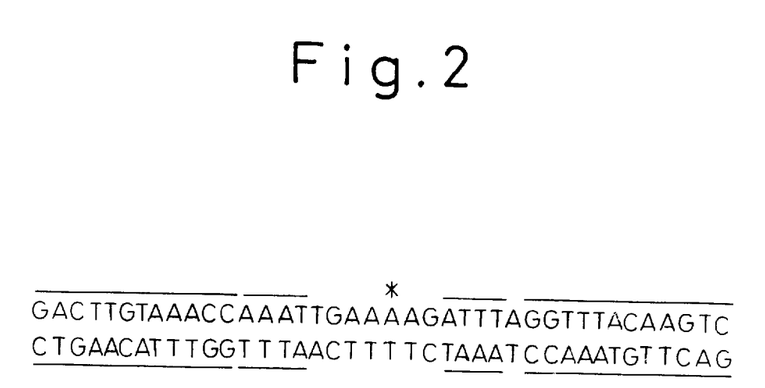
FIG. 2 shows a nucleotide sequence of the operator region of the biotin operon.

The "biotin operator region" of the biotin operon corresponds to a region from the −43rd to the −82nd position of FIG. 1, and forms an imperfect palindrome structure as shown in FIG. 2. This region is a so-called repressor protein-binding region, which forms, in the single strand state, a stable secondary structure by which the bases shown by the upper and lower lines form GC and AT pairs as the center base marked by *. It can be expected that a mutation, of the base pair within this region, especially the base pair taking the stem part shown by the upper and lower lines, more preferably the GC or CG base pair into some other base pair, permits the secondary structure in the single strand state to be changed to decrease the binding affinity with the repressor protein, resulting in the release of the reprssion of the expression to increase the transcription activity.

Table 1 shows the calculated minimum free energy of formation of the secondary structure in the single strand state within the operator region, when, in comparison with one in its wild type, one base pair conversion is brought about at G (GC pair in the state of double strand) and C (CG pair in the state of double strand), which are assumed to form a GC pair or CG pair having an especially strong binding force. The values for the minimum free energy were obtained by using the genetic information processing software GENETYX-CD (ver. 0.5, produced by Software Kaihatsu Kabushiki Kaisha). The mutation is represented as a pair in the double strand state.

TABLE 1

| Variation Site | Variation | Minimum Free Energy |
| --- | --- | --- |
| Wild type | None | −19.7 kcal/mol |
| −82 | GC → AT | −17.6 |
| −80 | CG → TA | −16.1 |
| −77 | GC → AT | −13.7 |
| −72 | CG → TA | −14.4 |
| −71 | CG → TA | −16.7 |
| −65 | GC → TA | −19.7 |
| −60 | GC → TA | −21.4 |
| −54 | GC → AT | −16.0 |
| −53 | GC → AT | −11.8 |
| −48 | CG → TA | −16.1 |
| −45 | GC → AT | −13.4 |
| −43 | CG → TA | −17.6 |

With respect to the mutation within the operator region, the conversion of the −77th GC pair into an AT pair, the conversion of the −65th GC pair into a TA pair, and the conversion of the −48th CG pair into a TA pair have been reported (*Nature*, 276, 689 (1978), *Gene*, 13, 89 (1981)). As is shown from Table 1, however, the GC→AT conversion at the −53rd base pair has the highest minimum free energy and, thus, it is most effective as the operator mutation.

Furthermore, this region overlaps with the rightward (bioB) promoter, and particularly a so-called −35 region (TTGTAA from the −79th to the −74th position of the right chain in FIG. 1) and the −10 region (also called Pribnow box, TAGGTT from the −56th to the −51st position of the right chain in FIG. 1), which are special nucleotide sequences associated with the recognition and binding of RNA polymerase, are particularly important. From the viewpoint of the degree of intensity of promotor activity, the sequence at the −35 region is preferably as similar as the sequence of TTGACA as a rule.

Although the conversion of the −77th GC pair into an AT pair has been reported as the mutation at this region, such a conversion is not preferable because this mutation is expected to significantly decrease the promotor activity. Next, as a rule, the sequence of Pribnow box is preferable as similar as the sequence of TATAAT. Considered together with the efficiency of the mutation of the operator, the mutation of the −54th GC pair into a TA pair and that of the −53rd GC into an AT pair are preferable. Among them, the mutation of the −53rd G→A is more preferable than that of the −54th G→T, taking into consideration the contribution to the increase in the promotor activity.

As described above, as is shown from Table 1, the mutation of the −53rd GC→AT, which has the highest minimum free energy, is most effective as the operator mutation, and also most effective in terms of increasing the rightward (bioB) promotor activity described above.

The sequence of GGAG from the −11th to the −8th region shown by underline in FIG. 1 is called an SD sequence (Shine—Dalgarno sequence). This sequence is a site at which the ribosomes are bound at a mRNA level, and the translation of the bioB gene initiates from the initiation codon ATG of the first position. The possibility of the region from the −6th to the 6th positions of the downstream of the SD sequence forming a firm secondary structure (a stem and loop structure), thereby decreasing the binding of ribosome to the SD sequence and the efficiency of initiating the translation from ATG, may be considered.

For this reason, by changing the stem part formed by the sequences of AGCC from the −6th to the −3rd positions and GGCT from the 3rd to the 6th positions by means of mutation, the bioB translation efficiency may be expected to be enhanced. Since the position of the stop codon and the region in the vicinity of the initiation codon are overlapped in the bioB, bioF, and bioC genes, it may be considered that if the translation efficiency of bioB is increased, the possibility of the translation efficiencies of bioF and bioC is also increased.

Considering that the GC pair is very firm in a single strand level, since the G residing on the −5th position, C on the −4th position, C on the −3rd position, or ATG of the initiation codon must be maintained, the change of the stem structure at this region can be more efficiently achieved by changing G on the 4th position, C on the 5th position, or the like into other bases. What is noted here is that a mutation in the bioB structural gene, i.e., the mutation of bases from the 4th to the 6th positions in this case, sometimes causes the exchange of amino acids. The event where this influence on the activity of bioB gene product itself, or this is associated with the stability of protein (intracellular lifetime) may be considered and, thus, the position of the mutation should be selected taking into consideration such events.

Process for Obtaining DNA Sequence of Biotin Operon According to the Present Invention The microorganisms which are used to obtain the biotin operon in which a mutation is induced at a specific position according to the present invention are biotin-producing bacteria of *Escherichia coli*, i.e., microorganisms possessing an enzymatic system for biotin biosynthesis and whose nucleotide sequence of the biotin operon regulatory region and the nucleotide sequence in the vicinity of the bioB initiation codon are shown in FIG. 1. They are not specifically limited as long as they are accorded to the object of the present invention, even if they possess any other properties. To be specific, any microorganism belonging to *Escherichia coli* which can advantageously be utilized for producing biotin may be used, possibly one possessing other drug resistance and effective characters, e.g., the character removed feedback repression by biotin is known in the art, at the same time.

Accordingly, as a parent strain of such a microorganism, any microorganism belonging to *Escherichia coli* may be utilized as long as it possesses a biotin biosynthetic pathway of biotin. Preferably, strains which have been previously mutated so as to be suitable for producing biotin, for example, DRK 3323 (FERM BP-2116) produced by the present inventors, in which the feedback repression by biotin having been released (see WO 89/4365) can be mentioned.

The DNA sequence of biotin operon according to the present invention can be obtained from the above parent strain using the following selection medium and method for selecting the desired mutant. For example, a process for obtaining the DNA sequence via the mutant having resistance to antimetabolite which is a biotin analogue can be mentioned. The biotin analogue to be used herein is a compound having a structure similar to biotin, and any biotin analogue can be used as long as it antagonizes against biotin and inhibits the growth of the microorganisms according to the invention. Examples include actithiazic acid (acidomycin, hereinafter abbreviated as "ACM"), α-dehydrobiotin, 5-(2-thienyl)valeric acid (hereinafter abbreviated as "TVA"), α-methyldesthiobiotin, α-methylbiotin, amicrenomycin, 4-imidazolidone caproic acid, homobiotin, norbiotin, and the like, but the biotin analogues are not limited thereto, and any other substance which meets the object of this invention can be used. They can be used alone or in combination of two or more.

Furthermore, as these substances, either those which are isolated from a culture of Actinomycetes, which produce and accumulate these substances, or those which are chemically sysnthesized, can be used. For example, ACM can be synthesized according to the method described by Clark, R. K., *Arch. Biochem. Biophys.*, 40, 270 (1952), and TVA can be synthesized according to the method described by Melville D. B., *J. Biol. Chem.* 146, 487, (1942).

For the medium utilized for the selection of mutants having resistance to these biotin analogues, e.g., resistance to ACM and TVA, it is desirable to use a minimum medium in which substances which are easily metabolized by the microorganisms to become energy sources or cell constructing components, for example, saccharides and glycerine for carbon sources, and organic substances such as peptones and yeast extracts for nitrogen sources, are used with limitation. When an appropriate minimum medium is used, not only ACM but also TVA can exhibit significant antimetabolizing action (for details of TVA, see Japanese Patent Application No. 2-235903) to decide the minimum inhibitory concentration for the microorganisms belonging to the usual genus Escherichia.

Onto a selection medium (agar plate medium) in which ACM and TVA are added to such a minimum medium in concentration of more than the minimum inhibitory concentrations, microorganisms belonging to the genus Escherichia, which have been subjected to a general mutagenesis treatment such as a mutagenesis treatment with a mutagen, such as N-methyl-N'-nitro-N-nitrosoguanine is applied and cultured. The resulting mutant colony having resistance to the ACM and TVA is collected with platinum loop, transferred to an appropriate biotin producing medium, and then cultured. The amount of biotin vitamers thus produced and accumulated were quantitatively determined, for example, by a bioassay using *Lactobacillus plantarum* as an indicator organisms. This is obtained by selecting a mutant having an increased capacity for producing biotin vitamers in comparison with the parent strain. The base sequence of the biotin operon regulatory region of this mutant or that in the vicinity of the bioB initiation codon of this mutant is sequenced and selected by comparing it with the nucleotide sequence of the one in its wild type strain, whereby a desired DNA can be obtained.

The determination of the nucleotide sequence at this region can be carried out by amplifying this region by the PCR (polymerase chain reaction) method using the chromosomal DNA of the mutant obtained by the above method as a template, and using an oligonucleotide primer which is complementarily synthesized against appropriate +chain and −chain interposing the nucleotide sequence of the biotin operon regulatory region or in the vicinity of the bioB initiation codon, and sequencing the amplified region by a dideoxy method [Messing,J; *Methods Enzymol.*, 101., 20 (1983)]. Alternatively, after all or part of the biotin operon containing the nucleotide sequence of the biotin operon regulatory region or in the vicinity of the bioB initiation codon has been previously cloned, the nucleotide sequence at this region may be determined by the dideoxy chain termination method.

Concrete examples of microorganisms having the biotin operon DNA sequence of this invention (hereinafter abbreviated as "DRAT strain") obtained as described above are *Escherichia coli* DRAT 9, DRAT 6, and DRAT 7 strains which were deposited at the Patent Microorganism Deposition Center of Fermentation Research Institute Agency of Industrial Science and Technology, in Japan, on Jul. 24, 1990 as FERM P-12378, P-12376, and P-12377, and then they transferred into it's International Depositary Authority and deposited under the Budapest Treaty, FERM BP-3990, BP-3988 and BP-3989, respectively.

Besides the above processes, the present invention can also be attained using a recombinant plasmid having, previously cloned biotin operon, e.g., pXBA 312 or pKHN 31, obtained by a plasmid extraction method known per se from, e.g., *Escherichia coli* DRK-3323 [pXBA 312] (FERM BP-2117) or DRK-332 [pKHN 31] (FERM BP-2114), to prepare a synthesized DNA having a nucleotide sequence of biotin operon regulatory region or in the vicinity of the bioB initiation codon according to the present invention.

In this case, it is desired that the synthesized DNA is designed so that it can easily be converted and inserted using an appropriate restriction enzyme site existing in the biotin operon. The synthesized DNA can advantageously be prepared either by a phosphoamidide method or phosphotriester method. The synthesis by a DNA automatic synthesizer using a phosphoamidide method is usual. Since the DNA is synthesized as a single strand, the complementary chain is always synthesized and annealed to use the DNA as a double strand. Moreover, using the cloned biotin operon described above the biotin operon of this invention can also be obtained by a site-directed mutagenesis [Kramer, W. et al.; *Method in Enzvmol.*, 154, 350 (1987)] with a synthesized oligonucleotide where the mutation according to this invention is introduced.

Not restricted to the point mutation, in the biotin operon DNA sequence of the present invention, a double mutation or greater may be constructed by the above methods, or other methods. For example, the biotin operon cloned from the DRAT 9 strain and the biotin operon cloned from the DRAT 6 or DRAT 7 strain may easily be recombined using the restriction enzyme Acc 1 site located in the biotin operon regulatory region shown in FIG. 1 to constitute a doubly mutated biotin operon.

Considering the availability in industry, the biotin operon DNA sequence of the invention can be utilized as a recombinant plasmid having a DNA sequence obtained from the DRAT strain, which is a microorganism containing the biotin operon of the invention, inserted in the vector DNA to introduce to any of the microorganisms belonging to the genus Escherichia, which can advantageously be used for producing biotin, as a host. This transformant generally exhibits high biotin-productivity. Consequently, another aspect of this invention, i.e., a process for producing biotin characterized by culturing microorganisms belonging to the genus Escherichia which has been transformed with the above plasmid, and collecting biotin from the culture broth, can be provided.

As milcroorganisms belonging to the genus Escherichia used as the host, any one can be used as long as it does not adversely affect the expression of biotin operon according to the present invention, the use of a strain that has previously undergone the mutation so as to be suitable for producing biotin, for example, the above-mentioned microorganism, DRAT strain, or DRK 3323 (FERM BP-2116), whose feedback repression by biotin has been released, prepared by the present inventors, is preferable. This is used to provide a process for producing biotin.

As the vector used herein, any commonly utilized vector, such as pBR 322 type plasmid, colicine (Col) E1 type plasmid, or lambda phage type using *Escherichia coli* as the host, may be applied. Because the biotin operon according to the present invention is a high expression system, a plasmid vector having a lower copying number corresponding to such a high expression, e.g., pMW 119 (produced by Nippon Gene Inc.), etc., can be used to save futile loading on the host, thereby providing a process for more advantageously producing biotin than the conventional process.

By the culture in such a nutrient medium under such conditions generally used for culturing a microorganism belonging to the genus Escherichia, the microorganism obtained as described above can accumulate a significant amount of biotin in the culture. For example, as the nutrient medium, any of the synthesized media and natural media containing carbon sources, nitrogen sources, and mineral substances known per se may be used. As carbon sources, carbohydrates, such as glucose, glycerine, fructose, sucrose, maltose, starches, starch hydrolyzed liquid syrups, or the like can be used. The amount used is preferably about 0.1 to 5.0%.

As nitrogen sources, various inorganic and organic ammonium salts, such as ammonia, ammonium chloride, ammonium phosphate, ammonium sulfate, and naturally originating nitrogen sources, such as amino acids, meat extracts, yeast extracts, corn steep liquors, casein hydrolyzed products, defatted soybean powder and digested products thereof, and the like may be used. The naturally originating nitrogen sources, in many cases, also serve as carbon sources, in addition to the nitrogen sources.

As the mineral substances, potassium dihydrogenphosphate, dipotassium hydrogenphosphate, magnesium sulfate, sodium chloride, copper sulfate, ferrous sulfate, manganese chloride, cobalt chloride, ammonium molybdate, boric acid, and the like can be used.

The addition of alanine described in EP-A-0316229 is also available in the microorganism of this invention. The amount to be added to the medium is suitably in the range of 1 to 10 g/l, and more preferably in the range of 3 to 7 g/l. Alanine may be initially added all at once or in several portions.

In the case where resistance to antibiotic for the prepared microorganism is imparted, the introduction of the corresponding antibiotic into the medium can make it possible to inhibit the incorporation of contaminating bacterium. The culture is preferably carried out under aerobic conditions, such as by shaking culture or aeration culture. The culture temperature is suitably 25°–37° C., and the pH level during the culture is preferably maintained around the neutral pH level. Usually, the period of the culture is approximately 24–72 hours. When biotin vitamers are collected from the culture broth after the completion of culturing, various properties of biotin vitamers, such as biotin and desthiobiotin, may be utilized to apply any of the various methods that are utilized in extraction and purification from general natural materials. For example, cells are removed from the culture broth, biotin vitamers are adsorbed on an activated carbon, followed by eluting them, and separating and purifying them with an ion-exchange resin. Alternatively, the filtrate from the culture broth can be directly treated with an ion-exchange resin to be separate and purified, and recrystallized from water or an alcohol. This can collect biotin vitamers such as biotin and desthiobiotin.

EXAMPLE

This invention will now be described in greater detail by referring to the following example, however, which are not intended to restrict the present invention.

Example 1

(1) Determination of the Minimum Inhibitory Concentration of ACM and TVA

*Escherichia coli* DRK-3323 strain (FERM BP-2116) was transferred with a platinum loop from an agar storage medium into a pyruvic acid minimum medium (8.8 g/l of sodium dihydrogenphosphate (12 hydrate), 1.2 g/l of dipotassium hydrogenphosphate, 1.0 g/l of ammonium sulfate, 0.1 g/l of magnesium sulfate (7 hydrate), 0.1 g of sodium pyruvate, adjusted to pH=7.0), and cultured by shaking at 37° C. for 16 to 18 hours. Thereafter, the bacterial cells were collected by centrifugation, repeatedly washed with the pyruvic acid minimum medium, and then resuspended in the same medium to prepare a suspension of bacterium to be inoculated. The suspension was inoculated with a pyruvic minimum medium media in which various concentrations of ACM or TVA had been added, and cultured at 37° C. for 24 hours. The amount of cells grown was quantitatively measured by turbidity (OD 660) to determine the effects of ACM and TVA on growth inhibition. The results are shown in Table 2 and Table 3. ACM inhibited the growth of DRK-3323 at the addition concentration of 0.1 g/l, and TVA inhibited the growth of DRK-3323 at the addition concentration of 2 g/l.

TABLE 2

| Concentration of Actithiazic Acid Added (g/l) | Cell Growth (OD660) |
| --- | --- |
| 0 | 0.42 |
| 0.01 | 0.40 |
| 0.05 | 0.38 |
| 0.1 | 0 |
| 0.2 | 0 |

TABLE 3

| Concentration of 5-(2-thienyl) Valeric Acid Added (g/l) | Cell Growth (OD660) |
|---|---|
| 0 | 0.42 |
| 0.125 | 0.41 |
| 0.25 | 0.40 |
| 0.5 | 0.35 |
| 1.0 | 0.08 |
| 2.0 | 0 |
| 4.0 | 0 |

(2) Preparation of Strains having Resistance to ACM and TVA

*Escherichia coli* DRK-3323 (FERM BP-2116) strain was cultured by shaking in a pyruvic acid minimum medium at 37° C. for 4 hours. After the cells at a logarithmic growth phase had been collected and washed, they were suspended in a TM buffer (0.61% Tris-base, 0.5% maleic acid, adjusted to pH 6.0) containing 100 μg/l of N-methyl-N'-nitro-N-nitrosoguanidine, and mutagenesis was carried out at 37° C. for 30 minutes. The cells collected and washed were subjected to recovery culture in the pyruvic acid minimum medium, and after collection and washing the suspension was applied on a pyruvic acid minimum agar plate medium containing 0.1 g/l of ACM and 2 g/l of TVA so that the number of cell was approximately $10^7$ per Petri dish. After culture at 37° C. for 48 hours, a colony ACM resistant mutant which appeared was collected by with platinum loop inoculated in an L medium (10 g/l peptone, 5 g/l of yeast extract, 1 g/l of glucose, 5 g/l of sodium chloride, adjusted to pH=7.0), and cultured at 37° C. for 48 hours. The amount of biotin produced and accumulated in the culture broth was quantitatively measured by a bioassay using *Lactobacillus plantarum* (ATCC 8014). As ACM resistant and TVA resistant strains having increased biotin production and accumulation capability, four strains, i.e., DRAT 6, DRAT 7, DRA 8, and DRAT 9, were obtained.

(3) Cloning of Biotin Operon from ACM Resistant and TVA Resistant Strains a) Preparation of Chromosomal DNA Each of the ACM resistant and TVA resistant strains obtained as described above was cultured by shaking in an L-medium (10 g/l peptone, 5 g/l of yeast extract, 1 g/l of glucose, 5 g/l of sodium chloride) at 37° C. for 48 hours. After the cells at a logarithmic growth phase had been collected and washed, they were extracted and purified by a usual DNA extraction method according to a phenol method (*Biochem, Biophys, Acta*, 72, 619 (1963)) to obtain a chromosomal DNA.

b) Preparation of Vector DNA

*Escherichia coli* DDK-3323 [pXBA 312] (FERM BP-2117) sufficiently grew in an L-medium having 10 μg/ml of tetracycline added thereto at 37° C., and plasmid pXBA 312 was obtained by a usual alkaline extraction method [*Nucleic acid Research*, 7, 1513 (1979)]. After being completely digested with the restriction enzyme, PstI, the present plasmid was subjected to a 1% agarose gel electrophoresis using agarose of low-melt temperature grade (produced by Bio-Rad). After being stained with ethidium bromide, the DNA segment of about 3.6 kb was cut off, heated at 70° C. for 5 minutes, a TE buffer- (10 mM tris hydrochloric acid, pH 8.0, 1 mM EDTA) saturated phenol was then added in an approximately equal amount, the mixture was well mixed, and then centrifuged to obtain an aqueous phase. A vector DNA was collected by ethanol precipitation from the aqueous phase.

c) Preparation of Recombinant Plasmid

Each of the chromosomal DNAs prepared in the above section (i) was completely cut with the restriction enzyme, PstI, subjected to an agarose electrophoresis, and DNA having a size of about 5.5 kb was collected in the same manner as that of the above-mentioned. Subsequently, the DNA was ligated to the vector DNA obtained from the section (ii) using a DNA ligation kit (produced by Takara Shuzo).

d) Screening

Each of the ligation solutions prepared in the above section (iii) was introduced to BR-4 strain, which is a biotin requiring strain mutated from *Escherichia coli* JA 221 described in Japanese Unexamined Patent Publication (Kokai) No. 62-155081 by a conventional calcium method [Mandel, M. et at., *J. Mol. Biol.*, 53, 109, (1970)]. The colony grown on a minimum agar plate medium having 10 μg of tetracycline added thereto without the addition of biotin (0.5% glucose, 0.4% ammonium sulfate, 0.2% potassium dihydrogenphosphate, 0.2% disodium hydrogenphosphate, 0.4% vitamin-free casamino acid, 0.002% tryptophan, 1.5% agar) sufficiently grew in an L-medium having 10 μg/ml of tetracycline added thereto at 37° C., and each of the plasmid DNAs was obtained by a usual alkali method.

From each of the extracted plasmids completely digested with two types of restriction enzymes, NcoI and EcoRI, the plasmid having the same direction of biotin operon insert as that of pXBA 312 was selected by observing the pattern of its agarose electrophoresis, whereby the recombinant plasmid pAMP 64 originating from DRAT 6, the recombinant plasmid pAMP 72 originating from DRAT 7 strain, the recombinant plasmid pAMP 82 originating from DRA 8 strain and the recombinant plasmid pAMP 912 originating from DRAT 9 strain were obtained, respectively.

(4) Determination of Nucleotide

The DNA sequences of biotin operon regulatory region and in the vicinity of the bioB initiation codon were determined by a dideoxy chain termination method [Messing, J., *Methods Enzymol.*, 101, 20 (1983)]. Into each of the restriction enzyme BamHI and SphI sites of M13 mpl8 RF DNA and M13 mpl9 RF DNA (purchased from Takara Shuzo) was inserted each of about 3.8 kb BamHI and SphI site fragments of each of the recombinant plasmids, pAMP 64, pAMP 72, pAMP 82, and pAMP 912 containing a DNA region of biotin operon regulatory region and in the vicinity of bioB initiation codon. *Escherichia coli* JM 105 cells which had been infected with each of the resulting recombinant phages were sufficiently grown in a 2×YT medium (1.6% bact-tripton, 1% bact-yeast extract, 0.5% sodium chloride) at 37° C. To the supernatant was added 17 volume % of 20% PEG (polyethylene glycol 6,000) –2.5N sodium chloride solution to precipitate phage. The precipitation was dissolved in a TE buffer, treated with phenol, and the aqueous phase was precipitated with ethanol. After centrifugation, for the single strand DNA solidified by drying, the reaction by the dideoxy chain termination method was carried out using an M13 sequence kit produced by Takara Shuzo and [α-32P]-dCTP (14.8 Tbq/mmol) produced by Amercham. The outline of this reaction is as follows:

The 17 b primer DNA (5'-CAGATATGGCGTTGGTC-3') corresponding to a part of the bioA coding region of *Escherichia coli* biotin operon was annealed to the above-mentioned single strand DNA (M13 mp 19 type). Separately, to the single strand DNA of M13 mp 18 type, the 17 b primer DNA (5'-ATTCTGTGACTTGCGAC) corresponding to a part of the bioB coding region of *Escherichia coli* biotin operon was similarly annealed. These two primers are just in the form where they interpose the biotin operon regulatory region. The DNA extension reaction from the primer was carried out using a Klenow enzyme. At this time, in order to be labeled with a radio isotope, [α-32P]-dCTP was incorporated. Moreover, for the purpose of chain termination, reaction systems, each containing ddATP, ddCTP, ddGTP, or ddTTP were prepared and then allowed to be reacted. One set, comprised of four reaction liquids each having the dideoxynucleotides added thereto, was subjected to an electrophoresis with an 8% polyacrylamide gel (40 cm, 0.3 mm thickness) containing 7.5M urea at a constant voltage of 200 V. After the electrophoresis, the gel was adhered on a Whattman 3 MM paper, dried in a gel drier produced by BioRad, and autoradiographed. It was then exposed at room temperature overnight using an X ray film produced by Fuji Film, and then developed. The results are shown in Table 4.

TABLE 4

| Origin of Biotin Operon | Mutation Site | Mutation Pattern |
| --- | --- | --- |
| DRAT 6 strain | 4 | GC → AT |
| DRAT 7 strain | −5 | GC → AT |
| DRA 8 strain | None within the region of this invention | None |
| DRAT 8 strain | −53 | GC → AT |

It can be understood from the above results that the biotin operons originating in DRAT 6, DRAT 7, and DRAT 9 are the biotin operons in accordance with the present invention.

Example 2

Production of Biotin Vitamers

The above-mentioned DRAT strains and BR-4 strains containing PAMP recombinant plasmid were transferred from an agar storage medium into an L-medium (having 20 μg/ml of tetracycline added thereto in the case of bacterial strain containing the recombinant plasmid) with a platinum loop to be cultured at 37° C. for 8 to 12 hours as a pre-culture 0.2 ml of each pre-cultured solution was inoculated in a 500 ml volume flask containing 20 ml of H-medium (17.6 g of disodium hydrogenphosphate (12 hydrate), 2.4 g/l of potassium dihydrogenphosphate, 4.0 g/l of ammonium sulfate, 10 g/l of yeast extract, 10 g of peptone, 0.1 g of ferrous sulfate (7 hydrate), 0.05 g/l of manganese chloride (4 hydrate), 0.1 g/l of magnesium sulfate (7 hydrate), 5.0 g/l of glucose, 5.0 g/l of DL-alanine, adjusted to pH=7.0), and a shaking culture was carried out at 37° C. for 24 hours, followed by the measurement of the amount of bacterial cells and the amount of biotin produced and accumulated. The results are shown in Table 5.

TABLE 5

|  | Name of Bacterium | Cell Growth (OD660) | Amount of Biotin Produced and Accumulated (mg/l) |
| --- | --- | --- | --- |
| Control | DRK-3323 | 12.0 | 0.39 |
|  | DRA 8 | 10.0 | 0.9 |
| Invention | DRAT 6 | 12.1 | 1.1 |
|  | DRAT 7 | 11.5 | 1.0 |
|  | DRAT 9 | 10.4 | 1.0 |
| Control | BR-4 [pXBA 312] | 13.3 | 2.7 |
|  | BR-4 [pAMP 82] | 13.6 | 2.6 |
| Invention | BR-4 [pAMP 64] | 12.2 | 6.6 |
|  | BR-4 [pAMP 72] | 13.1 | 6.8 |
|  | BR-4 [pAMP 912] | 13.5 | 10.0 |

We claim:

1. A mutated DNA sequence of the biotin operon of *Escherichia coli*, wherein the biotin operon contains at least one mutation of at least one position selected from the group consisting of −53, −5, and 4, taking the A of the ATG initiation codon of bioB and wherein the at least one mutation is a conversion of a GC pair to either an AT or TA pair.

2. A mutated DNA sequence according to claim 1, wherein the at least one mutation is a conversion of a GC pair to an AT pair.

3. A process for producing biotin characterized by cultivating microorganisms belonging to genus Escherichia having been transformed with recombinant plasmid carrying the DNA sequence of claim 1 in a nutrient medium, and collecting biotin from the culture broth.

* * * * *

UNITED STATES PATENT AND TRADEMARK OFFICE
CERTIFICATE OF CORRECTION

PATENT NO.   : 5,885,792
DATED        : March 23, 1999
INVENTOR(S)  : Ohji Ifuku, et al.

It is certified that error appears in the above-identified patent and that said Letters Patent is hereby corrected as shown below:

Title page, item [73], Assignee: after "Shiseido Company, Ltd.., Tokyo, Japan" insert --Takeda Chemical Industries, Ltd., Osaka, Japan--

Signed and Sealed this

First Day of August, 2000

*Attest:*

Q. TODD DICKINSON

*Attesting Officer*   Director of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Escherichia coli     ( x i ) SEQUENCE DESCRIPTION: SEQ ID NO:1:

```
C A G A T A T G G C   G T T G G T C                                    1 7
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Escherichia coli     ( x i ) SEQUENCE DESCRIPTION: SEQ ID NO:2:

ATTCTGTGAC TTGCGAC        17

( 2 ) INFORMATION FOR SEQ ID NO:3:

( i ) SEQUENCE CHARACTERISTICS:
        ( A ) LENGTH: 114 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Escherichia coli     ( x i ) SEQUENCE DESCRIPTION: SEQ ID NO:3:

CGTCCGTTGT CATAATCGAC TTGTAAACCA AATTGAAAAG ATTTAGGTTT ACAAGTCTAC    60

ACCGAATTAA CAACAAAAAA CACGTTTTGG AGAAGCCCCA TGGCTCACCG CCCA    114

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Escherichia coli     ( x i ) SEQUENCE DESCRIPTION: SEQ ID NO:4:

GACTTGTAAA CCAAATTGAA AAGATTTAGG TTTACAAGTC    40